United States Patent
Tinari

(10) Patent No.: US 11,613,844 B1
(45) Date of Patent: Mar. 28, 2023

(54) METHOD FOR ADDING AROMATICS TO A FACE COVERING

(71) Applicant: Colleen Tinari, Weeki Wachee, FL (US)

(72) Inventor: Colleen Tinari, Weeki Wachee, FL (US)

( * ) Notice: Subject to any disclaimer, the term of this patent is extended or adjusted under 35 U.S.C. 154(b) by 413 days.

(21) Appl. No.: 17/002,312

(22) Filed: Aug. 25, 2020

(51) Int. Cl.
| | |
|---|---|
| *D06B 1/02* | (2006.01) |
| *D06M 13/00* | (2006.01) |
| *A61M 21/00* | (2006.01) |
| *D06M 13/165* | (2006.01) |
| *C09D 105/16* | (2006.01) |
| *D06M 101/34* | (2006.01) |

(52) U.S. Cl.
CPC .......... *D06M 13/005* (2013.01); *A61M 21/00* (2013.01); *C09D 105/16* (2013.01); *D06B 1/02* (2013.01); *D06M 13/165* (2013.01); *A61M 2021/0016* (2013.01); *A61M 2210/0618* (2013.01); *D06B 2700/27* (2013.01); *D06M 2101/34* (2013.01)

(58) Field of Classification Search
CPC ....... D06M 13/005; A61M 21/00; D06B 1/02; C09D 105/16
See application file for complete search history.

(56) References Cited

U.S. PATENT DOCUMENTS

| | | | |
|---|---|---|---|
| 2005/0060811 A1* | 3/2005 | Smith ................ | D06M 13/005 8/115.51 |
| 2006/0045860 A1* | 3/2006 | Gupta ................ | A61K 8/0212 424/442 |
| 2009/0084384 A1* | 4/2009 | Cheng ................ | A62B 23/025 128/206.19 |

* cited by examiner

*Primary Examiner* — Nathan T Leong
(74) *Attorney, Agent, or Firm* — Gulf Coast Intellectual Property Group

(57) ABSTRACT

A method for infusing an aromatic essential oil into a face covering so as to provide a prolonged olfactory benefit to the wearer of the face covering. The method of the present invention includes utilization of specific unit volumes of an essential oil, a carrier oil and a cyclodextrin wherein the aforementioned are placed into a suitable container that is located in a temperature controlled environment. The ingredients are mixed so as to initiate the emulsification process and as such encapsulation of the oil components occurs. A dry sprayer is utilized to apply a portion of the mixture onto the face covering and immediately thereafter the face covering is placed in a storage container. The carrier oil is maintained at a temperature during introduction into the mixing container. The method of the present invention provides an olfactory release for an extended period of at least 12 hours.

12 Claims, 2 Drawing Sheets

FIG. 2

- 201 Place Container
- 203 Deposit Essential Oil
- 205 Add Carrier Oil
- 207 Place B-Cyclodestrin
- 209 Blend Mixture
- 211 Encapsulattion Period
- 213 Stir Mixture
- 215 Deposit Portion into Sprayer
- 217 Infuse Mask
- 219 Cure Mask

100

METHOD FOR ADDING AROMATICS TO A FACE COVERING

FIELD OF THE INVENTION

The present invention relates generally to personal protection equipment, more specifically but not by way of limitation, a method of infusing aromatics into personal protective equipment such as but not limited to face coverings.

BACKGROUND

As is known in the art, personal protective equipment covers a broad range of articles that are designed to provide varying degrees of protection for the wearer. Personal protective equipment includes articles such as but not limited to gloves, aprons and masks. For the latter, the masks are typically worn on the face and constructed so as to provide coverage of both the mouth and the nose. Conventional face masks are manufactured of breathable material but are constructed so as to inhibit passage of particles of varying sizes. Different face masks have different ratings such as but not limited to N95 which refers to the size of particle that is blocked by the face mask. Regardless of the effective rating of the face mask, most are manufactured from a cloth, nylon or other type of similar material.

Existing global conditions have resulted in the requirement to wear a face mask for the general public. While previously worn by healthcare workers and a few other industries, it is now common practice to wear, or be required to wear a face mask when out in public. This requirement causes some inconveniences for the wearers as well as some general unpleasantries. As traditional masks will inhibit complete and effective evacuation of exhalation of the wearer, unpleasant odors can be one inconvenience of wearing a mask.

It is intended within the scope of the present invention to provide a method for infusing an essential oil, such as but not limited to peppermint oil, into material utilized to construct face masks wherein the essential oil provides a beneficial olfactory experience for the wearer of the face mask.

SUMMARY OF THE INVENTION

It is the object of the present invention to provide a method for adding an aromatic to a face mask or similar material so as to provide a beneficial olfactory experience for the wearer wherein the method of the present invention infuses an essential scented oil into the face mask.

Another object of the present invention is to provide a method for introducing a fragrant essential oil into a face mask wherein the method of the present invention includes the encapsulation of an essential oil with a starch.

A further object of the present invention is to provide a method for adding an aromatic to a face mask or similar material so as to provide a beneficial olfactory experience for the wearer that further includes the step of controlling the temperature during emulsification of the essential oil.

Still another object of the present invention is to provide a method for introducing a fragrant essential oil into a face mask wherein the method of the present invention further includes utilization of a carrier oil.

An additional object of the present invention is to provide a method for adding an aromatic to a face mask or similar material so as to provide a beneficial olfactory experience for the wearer wherein an emulsified mixture is introduced into the face mask material utilizing dry spray atomization.

Yet a further object of the present invention is to provide a method for introducing a fragrant essential oil into a face mask wherein the method of the present invention further includes curing the face mask in a container.

Another object of the present invention is to a provide a method for adding an aromatic to a face mask or similar material so as to provide a beneficial olfactory experience for the wearer wherein the method of the present invention includes controlling the temperature of the carrier oil and essential oil.

An alternate object of the present invention is to provide a method for introducing a fragrant essential oil into a face mask wherein the method provides a face mask that delivers an improved olfactory benefit for at least eight hours.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

FIG. 2 is a flowchart of the process of the present invention.

DETAILED DESCRIPTION

Figure 1:
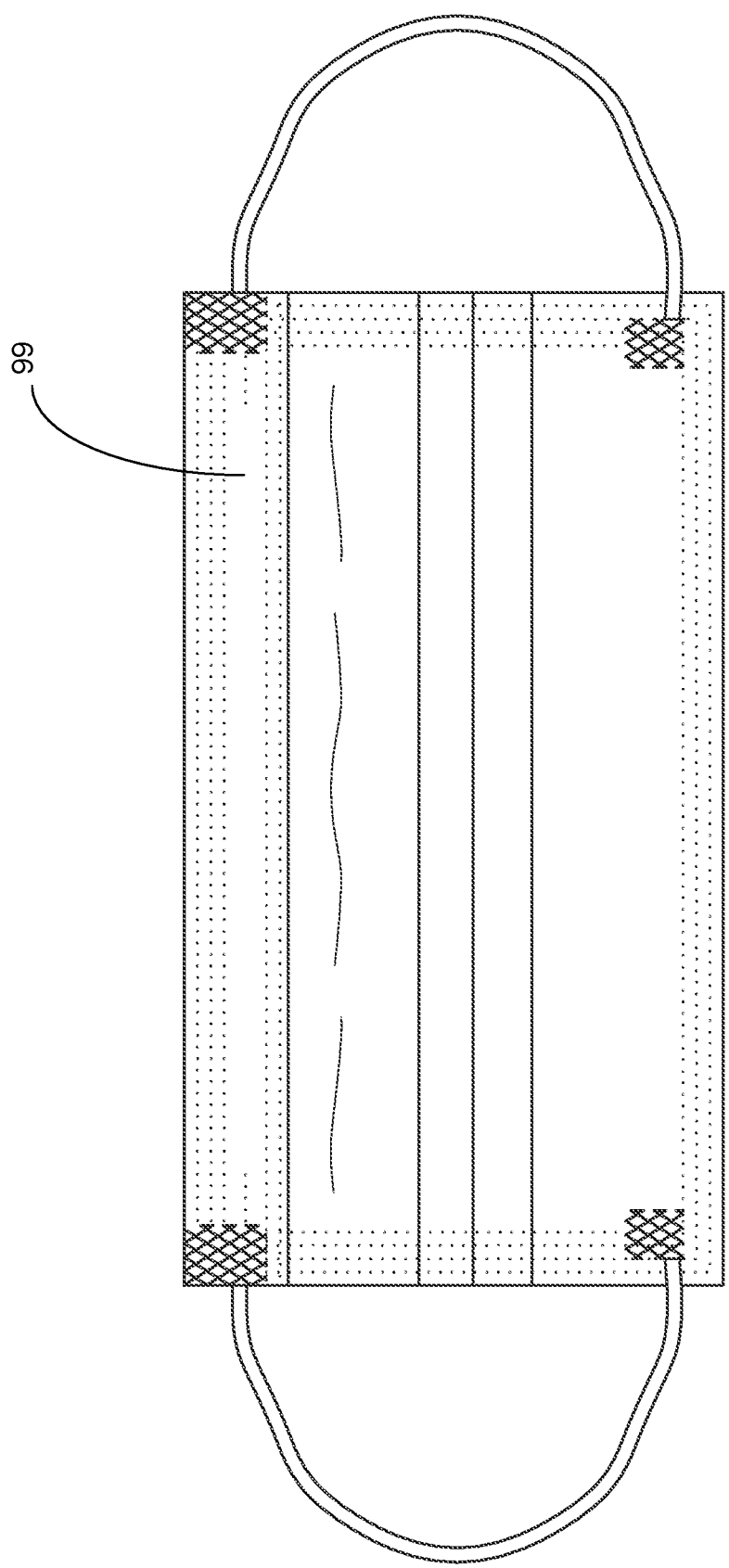
FIG. 1 is a front view of an exemplary face covering.

Referring now to the drawings submitted herewith, wherein various elements depicted therein are not necessarily drawn to scale and wherein through the views and figures like elements are referenced with identical reference numerals, there is illustrated a method for adding aromatics to a face covering 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Now referring in particular to the Figures submitted as a part hereof, the method for adding aromatics to a face covering 100. Illustrated herein in FIG. 1 is an exemplary face covering 99. The face covering is manufactured from a material such as but not limited to cloth, nylon or blend of other suitable materials to achieve the desired objective of providing air filtration for a user. The face covering 99 is exemplary only and it should be understood within the scope of the present invention that the present invention could be utilized to infuse aromatics into numerous styles and shapes of face coverings. Furthermore, while the preferred embodiment of the present invention is focuses on infusing aromatics into exemplary face covering 99, it is contemplated within the scope of the present invention that the present invention could be employed to infuse aromatics into other materials and/or personal protective equipment.

Now referring in particular to FIG. 2 herein, a flow chart of the method of the present invention is diagrammed therein. The present invention is operable to introduce aromatic essential oils into the material of the exemplary face covering and provide stability once infused in order to deliver an olfactory benefit to a user for an extended period of time. In step 201, a suitable container is placed in a climate-controlled room. The climate controlled room is maintained at a temperature of approximately 74 degrees during execution of the method of the present invention as described herein. While 74 degrees is the preferred temperature, good results have been achieved maintaining a temperature range of 72 to 76 degrees. In a preferred embodiment the container is a non-reactive container such as but not limited to stainless steel. Step 203, 1.75 units of essential oil is deposited within the interior volume of the container. It should be understood within the scope of the present invention that a unit could be various alternate volume measurements such as but not limited to an ounce or a gallon. In step 205, 1.0 units of a carrier oil is added into the container oil. It is contemplated within the scope of the present invention that various alternate type of carrier oil, also referred to as base oils could be utilized. By way of example but not limitation, a vegetable oil could be utilized as the carrier oil. During execution of step 205, the carrier oil has been maintained at a temperature range between 89 to 90 degrees. While the aforementioned temperature range is preferred, good results have been achieved by utilizing a temperature range between 85 and 95 degrees for the carrier oil.

Step 207, 1 unit of b-cyclodextrin is placed into the container. In step 209, the mixture present in the container is blended for approximately ten seconds. This emulsification procedure initiates the adherence of the b-cyclodextrin to the oil components of the mixture and as such provides encapsulation thereof. Step 211, the mixture is provided a resting period of at least two minutes. The resting period provides sufficient time to allow the b-cyclodextrin to fully encapsulate the oils in the mixture. It should be understood within the scope of the present invention that the resting period could be longer than two minutes. Additionally, while b-cyclodextrin is the preferred oligosaccharide for the present invention, it is contemplated within the scope of the present invention that alternate cyclodextrins could be employed in the process of the present invention. In step 213, ensuing the encapsulation period, the mixture is stirred for approximately ten to fifteen seconds.

Step 215, ensuing completion of the preparation of the mixture, a portion thereof is deposited into a dry spray atomizer. It should be understood within the scope of the present invention that the dry spray atomizer is a conventional dry sprayer that emits the mixture in small particles so as to facilitate the penetration of the mixture particles into the fiber crevices of the material of the exemplary face mask 99. While no particular pressure of the dry sprayer is required, good results have been achieved utilizing a pressure range of 20 to 25 PSI for the dry sprayer. In step 217, the dry sprayer is utilized to deposit the mixture onto the exemplary face mask 99. Step 219, the exemplary mask 99 is placed in a sealable container for curing. The curing process occurs for at least twelve hours but it is contemplated within the scope of the present invention that the curing time for best results should be between twelve and thirty-six hours. The curing process occurs in a sealable container wherein the preferred embodiment of the sealable container is an odor resistant, food grade plastic waterproof sealed bag. While the aforementioned is the preferred container for curing, it is contemplated within the scope of the present invention that alternate containers could be employed to store the exemplary masks for curing.

While a specific unit volume of the carrier oil, essential oil and b-cyclodextrin have been discussed herein, it is contemplated within the scope of the present invention that alternate ratios could be employed to manufacture the mixture of the present invention.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding description is, therefore, not intended to be limited to the specific forms set forth herein, but on the contrary, it is intended to cover such alternatives, modifications, and equivalents, as can be reasonably included within the spirit and scope of the invention.

What is claimed is:

1. A method of infusing an aromatic essential oil into a fabric comprising the steps of:
    depositing a volume of essential oil into a container, wherein the essential oil is a volatile aromatic oil;
    placing a volume of carrier oil into the container;
    adding a volume of cyclodextrin into the container;
    blending the essential oil, carrier oil and cyclodextrin in the container to create a mixture;
    allowing the mixture to rest in the container;
    placing a portion of the mixture into a dry sprayer;

applying the mixture to a fabric utilizing the dry sprayer; and storing the fabric in a sealable container for curing.

2. The method of infusing an aromatic essential oil into a fabric as recited in claim 1, wherein the carrier oil volume is one unit of a measured amount.

3. The method of infusing an aromatic essential oil into a fabric as recited in claim 2, wherein the essential oil volume is 1.75 units of the measure amount.

4. The method of infusing an aromatic essential oil into a fabric as recited in claim 3, wherein the cyclodextrin is one unit of a measure amount.

5. The method of infusing an aromatic essential oil into a fabric as recited in claim 4, and further including the step of maintaining the carrier oil at a temperature range of 85 to 95 degrees.

6. The method of infusing an aromatic essential oil into a fabric as recited in claim 5, wherein the cyclodextrin is b-cyclodextrin.

7. The method of infusing an aromatic essential oil into a fabric as recited in claim 6 and further including the step of controlling a temperature in an environment in which the container is disposed.

8. The method of infusing an aromatic essential oil into a fabric as recited in claim 7, wherein the temperature of the environment of the container is maintained at a temperature between 72 and 76 degrees.

9. A method of infusing a face covering with an aromatic essential oil in order to provide an olfactory benefit to a wearer of the face covering wherein the method of the present invention comprises the steps of:

placing a container in a temperature controlled environment, wherein the temperature controlled environment is maintained at a temperature between 72 and 76 degrees;

depositing a 1.75 unit volume of essential oil into the container, wherein the essential oil is a volatile aromatic oil;

placing 1 unit volume of carrier oil into the container;

adding 1 unit volume of cyclodextrin into the container;

blending the essential oil, carrier oil and cyclodextrin in the container to create a mixture, wherein the mixture is blended for at least fifteen seconds;

allowing the mixture to rest in the container, wherein the mixture is allowed to rest in the container for at least two minutes;

placing a portion of the mixture into a dry sprayer;

applying the mixture to a fabric utilizing the dry sprayer wherein the dry sprayer utilizes a pressure between 20 and 25 PSI; and storing the fabric in a sealable container for curing.

10. The method of infusing a face covering with an aromatic essential oil as recited in claim 9, and further including the step of maintaining the carrier oil at a temperature range of 85 to 95 degrees.

11. The method of infusing a face covering with an aromatic essential oil as recited in claim 10, wherein the cyclodextrin is b-cyclodextrin.

12. The method of infusing a face covering with an aromatic essential oil as recited in claim 11, wherein the face coverings are cured for at least 12 hours.

* * * * *